(12) United States Patent
Lee et al.

(10) Patent No.: US 6,562,980 B1
(45) Date of Patent: May 13, 2003

(54) METHOD FOR PRODUCING 5-ARYLOXYMETHYL-2-OXAZOLIDINONES

(75) Inventors: Fang-Yu Lee, Taichung (TW); Tsang-miao Huang, Chunghua (TW); Chao-Ho Chung, Hsinchu (TW)

(73) Assignee: Yung Shin Pharma Ind. Co., Ltd., Taichung (TW)

( * ) Notice: Subject to any disclaimer, the term of this patent is extended or adjusted under 35 U.S.C. 154(b) by 0 days.

(21) Appl. No.: 10/222,797

(22) Filed: Aug. 19, 2002

(51) Int. Cl.[7] .............................................. C07D 63/06
(52) U.S. Cl. .................................................... 548/232
(58) Field of Search ................................. 548/215, 225, 548/232; 544/113

(56) References Cited

U.S. PATENT DOCUMENTS

| 2,895,960 A | 7/1959 | Lunsford |
| 3,062,827 A | 11/1962 | Lunsford |

FOREIGN PATENT DOCUMENTS

| WO | WO 860681 | * 7/1986 |

OTHER PUBLICATIONS

Lunsford, C.D.; 5–Aryloxymethyl–2–oxazolidinones; Chemical Research Laboratory; vol. 82, p. 1166–1171.
John R. Stanko, 1990, Williams & Wilkins, "Oral skeletal muscle relaxants", The journal of Craniomandibular Practice, 8(3): 235–243.*

* cited by examiner

Primary Examiner—Joseph K. McKane
Assistant Examiner—Rei-Tsang Shiao
(74) Attorney, Agent, or Firm—Fei-Fei Chao; Venable, Baetjer, Howard & Civiletti, LLP

(57) ABSTRACT

The present invention provides a method for making 5-aryloxymethyl-2-oxazolidinone and derivatives thereof having the general formula of:

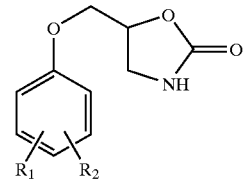

wherein $R_1$ and $R_2$ are hydrogen, alkyl, or alkoxyl group and wherein the alkyl or alkoxyl group contains no more than three carbon atoms in straight or branched chain. The invention involves the fusion of a triglycidyl isocyanurate (TGIC) with an unsubstituted or a mono- or di-substituted phenol.

17 Claims, 3 Drawing Sheets

METHOD FOR PRODUCING 5-ARYLOXYMETHYL-2-OXAZOLIDINONES

FIELD OF THE INVENTION

The present invention relates to a method for making 5-aryloxymethyl-2-oxazolidinones having the general formula (I) of:

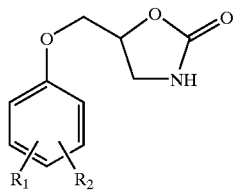

(I)

wherein $R_1$ and $R_2$ are hydrogen, halogen, alkyl, or alkoxyl group and wherein the alkyl or alkoxyl group contains no more than three carbon atoms in straight or branched chain. In particular, the invention relates to a method for synthesizing 5-aryloxymethyl-2-oxazolidinones by reacting a triglycidyl isocyanurate (TGIC) with an unsubstituted or a mono- or di-substituted phenol.

BACKGROUND OF THE INVENTION

5-Aryloxymethyl-2-oxazolidinones are a group of compounds which is well-known in having activity as interneuronal blocking agents or depressants of central synaptic transmission. The compounds have the general formula of:

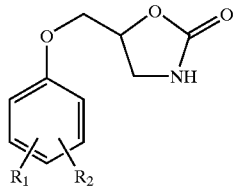

(I)

where $R_1$ and $R_2$ can be hydrogen, halogen, alkyl, or alkoxyl group.

These compounds, characterized by the presence of specific substituents in specific positions on the phenyl ring, have been found to have superior activity on blocking the abnormal nervous impulses which give rise to spasm. They are generally antagonists of strychnine convulsions and have been for use as skeletal muscle relaxants, anticonvulsants, and tranquilizers.

Two particular compounds of this group, metaxalone and mephenoxalone, are especially useful for their skeletal muscle relaxant and/or anxiolytic effects. Metaxalone, having the chemical name of 5'-(3,5-dimethylphenoxymethyl)-2-oxazolidinone, is a skeletal muscle relaxant. It acts in the central nervous system (CNS) to produce the muscle relaxant effects. The chemical structure of metaxalone is shown as formula (II):

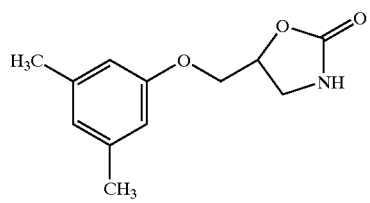

(II)

Metaxolone is currently commercially available in the U.S. under the tradename of Skelaxin® (as a 400 mg, pale rose, scored tablet) and distributed by Elan Pharmaceuticals (Cedar Knolls, N.J.). According to the statements in Skelaxin® package insert, the mechanism of action of metaxalone in humans has not been established, but may be due to general central nervous system depression. It has no direct action on the contractile mechanism of striated muscle, the motor end plate or the nerve fiber. Skelaxin® is indicated as an adjunct to rest, physical therapy, and other measures for the relief of discomforts associated with acute, painful musculoskeletal conditions.

Mephenoxalone, having the chemical name of 5-(2-methoxyphenoxy)methyl)-2-oxazolidinone, is a skeletal muscle relaxant, is a skeletal muscle relaxant as well as an anxiolytic. The chemical structure of mephenoxalone is shown as formula (III):

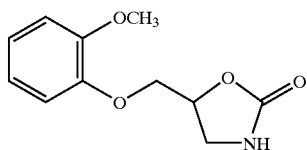

(III)

The method for making mephenoxalone (5-o-methoxyphenoxymethyl-2-oxazolidone) is disclosed in U.S. Pat. No. 2,895,960, issued to Lunsford et al. The method involves a fusion of about 1 mol equivalents of urea with about 1 mol equivalent of 3-o-methoxyphenoxy-2-hydroxy-1-propyl carbamate (FIG. 1). The reactants are commercially available. The method described in U.S. Pat. No. 2,895,960 produces a crude oxazolidone, which may be further purified by fractional distillation or recrystallization.

Metaxalone can be produced by the method described in U.S. Pat. No. 3,062,827, issued to Lunsford et al. The patent discloses generally the process of making 5-(3,5-dialkylphenoxymethyl)-2-oxazolidones which involves a fusion of a selected 3-phenoxyl-1,2-propanediol (having the predetermined substituents on the phenyl ring) with urea at a 1:2 molar ratio, with or without a solvent (FIG. 2). Alternatively, a selected 3-phenoxy-1-chloro-2-propanol may be reacted with urea instead of the phenoxy-1,2-propanediol, using the same molar ratios and under the same reaction conditions. Furthermore, the 5-(3,5-dialkylphenoxymethyl)-2-oxazolidones may be prepared by reacting a selected 3-phenoxy-2-hydroxy-1-propyl-carbamate and urea. The method described in U.S. Pat. No. 3,062,827, similar to that of U.S. Pat. No. 2,895,960, produces a crude oxazolidone, which requires further purification by fractional distillation or recrystallization.

Lunsford et al., *J. Am. Chem. Soc.* (1960), 82:1166–1171, further explores the sequence of reaction for making 5-aryloxymethyl-2-oxazolidinones as described in U.S. Pat. Nos. 2,895,960 and 3,062,827. Its finding confirms that in order to locate unequivocally the aryloxymethyl group of the compounds at position 5 (rather than position 4) of the oxazolidinone ring, the reaction should be subject to basic hydrolysis which gives rise to a 1-amino-3-(o-methoxyphenoxy)-2-propanol, which is then fused with urea to produce 5-aryloxymethyl-2-oxazolidinones.

In the invention to be presented in the following sections, a novel method for synthesizing a 5-aryloxymethyl-2-oxazolidinone by fusing about 1 molar equivalent of a triglycidyl isocyanurate (TGIC) with 3 molar equivalents of a substituted phenol is introduced. The present method differs from the prior art methods particularly for its use of different starting materials and different molar ratios of the reactants.

SUMMARY OF THE INVENTION

The present invention provides a process for preparing 5-aryloxymethyl-2-oxazolidinones having the general formula (I) of:

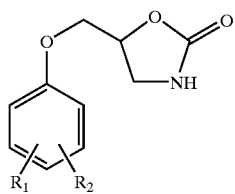

(I)

in which $R_1$ and $R_2$ are hydrogen, halogen, alkyl, or alkoxyl group and in which the alkyl or alkoxyl group contains no more than 3 carbon atom in straight or branched chain.

The process includes a reaction between a triglycidyl isocyanurate (TGIC) of formula (IV):

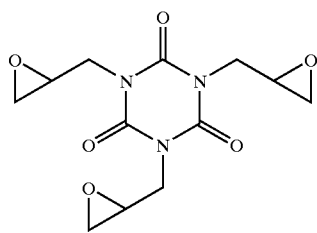

(IV)

and an unsubstituted or a mono- or di-substituted phenol of formula (V):

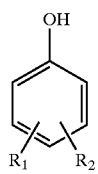

(V)

wherein $R_1$ and $R_2$ are the same as those shown in formula (I). Preferably, the reaction is performed in the presence of a base. The preferred examples of base include, but are not limited to, NaOH and $NH_4OH$, and most favorably, NaOH. The preferred molar ratio of TGIC and the unsubstituted or substituted phenol is about 1:3.

5-Aryloxymethyl-2-oxazolidinones are compounds that can be used as anticonvulsants, muscle relaxants, tranquilizers, and/or anxiolytics in humans. Examples of 5-aryloxymethyl-2-oxazolidinones include metaxolone, which is 5-(3,5-dimethylphenoxymethyl)-2-oxazolidinone; and mephenoxalone, which is 5-(2-methoxyphenoxy) methyl)-2-oxazolidinone. Both metaxolone and mephenoxalone are skeletal muscle relaxants. Mephenoxalone is also an anxiolytic.

TGIC and the unsubstituted or mono- or di-substituted phenol are perferred to be dissolved in a solvent and reacted under reflux condition. Examples of the solvent that can be used in the process include, but is not limited to, acetone, ethanol, chloroform, and ethyl acetate. The preferred solvent is acetone, which can be used in combination with water.

The process is also preferably performed under anaerobic condition such as carrying out under nitrogen gas. The time required for complete reaction is about 10 to 60 hours, preferably 12 to 24 hours.

After the completion of the reaction, the crude 5-aryloxymethyl-2-oxazolidinone is further purified by partitioning the crude 5-aryloxymethyl-2-oxazolidinone between a water layer and an ethyl acetate layer. The purified 5-aryloxymethyl-2-oxazolidinone is recovered from the ethyl acetate layer. The preferred volume ratio between the ethyl acetate layer and the water layer is about 50:30. Preferably, the partitioning step is repeated three times. The purified 5-aryloxymethyl-2-oxazolidinone is collected from the ethyl acetate layer by letting the ethyl acetate layer sit for a suitable period of time to allow precipitation of the purified 5-aryloxymethyl-2-oxazolidinone. The precipitant is then collected by filtration and dried, using conventional methods. The purified 5-aryloxymethyl-2-oxazolidinone is in white, powdery form.

The present invention also provides a method for relieving patients with musculoskeletal discomforts by administering the 5-aryloxymethyl-2-oxazolidinone prepared by the method as described above to the patients. Examples of the 5-aryloxymethyl-2-oxazolidinone includes, but is not limited to, metaxolone or mephenoxalone. The 5-aryloxymethyl-2-oxazolidinone is preferred to be orally administered to patients, such as in the form of tablets or capsules.

The reaction involved the fusion of triglycidyl isocyanurate (TGIC) with an unsubstituted or substituted phenol in a molar ratio of approximately 1:3. The reaction was conducted in the presence of NaOH. The reactants were dissolved in acetone and under reflux condition.

DETAILED DESCRIPTION OF THE INVENTION

The traditional way for making 5-aryloxymethyl-2-oxazolidinones requires the reaction of a selected 3-phenoxy-1,2-propanediol or 3-phenoxy-2-hydroxy-1-propylcarbamate with urea with or without a solvent, as indicated in U.S. Pat. Nos. 2,894,960 and 3,062,827. The reaction requires heating the reactants at an elevated temperature, usually at 170° C. to 200° C., and preferably at about 185° C., with constant stirring. The resulting crude oxazolidinone may be purified by extraction with a solvent such as chloroform or ethyl acetate and fractionally distilling to recover the pure oxasolidone product. This method yields about 55% to 60% of pure oxazolidinone. A second method requires recrystallization of the crude oxazolidinone from an oxygenated solvent, e.g., alcohols such as ethyl alcohol and ketones such as acetone and water. This method yields of about 40% of pure oxazolidinones.

The present invention uses entirely different starting materials to make 5-aryloxymethyl-2-oxazolidinones. The reactants are triglycidyl isocyanurate (TGIC) and an unsubstituted or substituted phenol. Both are commercially available.

Triglycidyl isocyanurate (TGIC) is a synthetic white powder or granule with no discernible odor at room temperature. It is usually used as a three-dimensional cross-linking or curing agent in polyester powder coatings (paints). TGIC, in its molten state, reacts easily with various functional groups in the presence of catalysts or promoters. TGIC, like other similar epoxides, can react with amines, carboxylic acids, carboxylic acid anhydrides, phenols and alcohols. Commercial (technical) grade TGIC is a mixture of two optical stereoisomers, $\alpha$ and $\beta$. The $\alpha$ isomer has been used as an experimental anti-tumor agent. TGIC ($\alpha$ form) melts at 105° C. while the $\beta$ form melts at 156° C. The two main technical grades of TGIC can be purchased from Ciba-Geigy Pty Ltd., Switzerland and Nissan Chemical Industries Pty Ltd., Japan.

Phenol is a colorless to light pink crystalline compound. The selected substituted phenol is commercially available and also can be prepared by conventional methods.

The process of the present invention is highly desirable, particularly because of its simple chemical reaction and easy purification step, which in turn substantially reduces the costs of manufacturing the compounds and increases the product yield.

Figure 1:
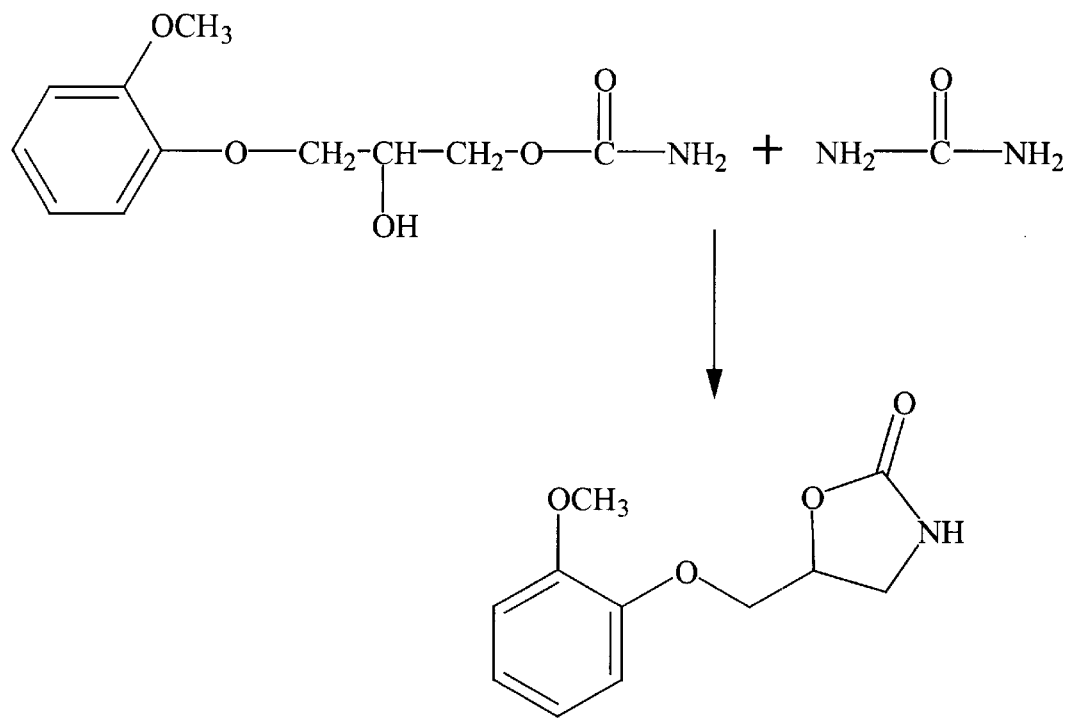
FIG. 1 (prior art) shows a reaction process for making 5-o-methoxyphenoxymethyl-2-oxaxolidinone. The reaction scheme is disclosed in U.S. Pat. No. 2,895,960. The reaction involves the fusion of about 1 molar equivalent of urea with 1 molar equivalent of 3-o-methoxyphenoxy-2-hydroxy-1-prophyl carbamate. The reactants are commercailly available. 3-o-methoxyphenoxy-2-hydroxy-1-prophyl carbamate may be prepared by reacting 3-o-methoxyphenoxy-1,2-propanediol with phosgene to produce the intermediate chlorocarbonate compound and then reacting the chlorocarbonate with ammonium hydroxide to yield the desired carbamate.
Figure 2:
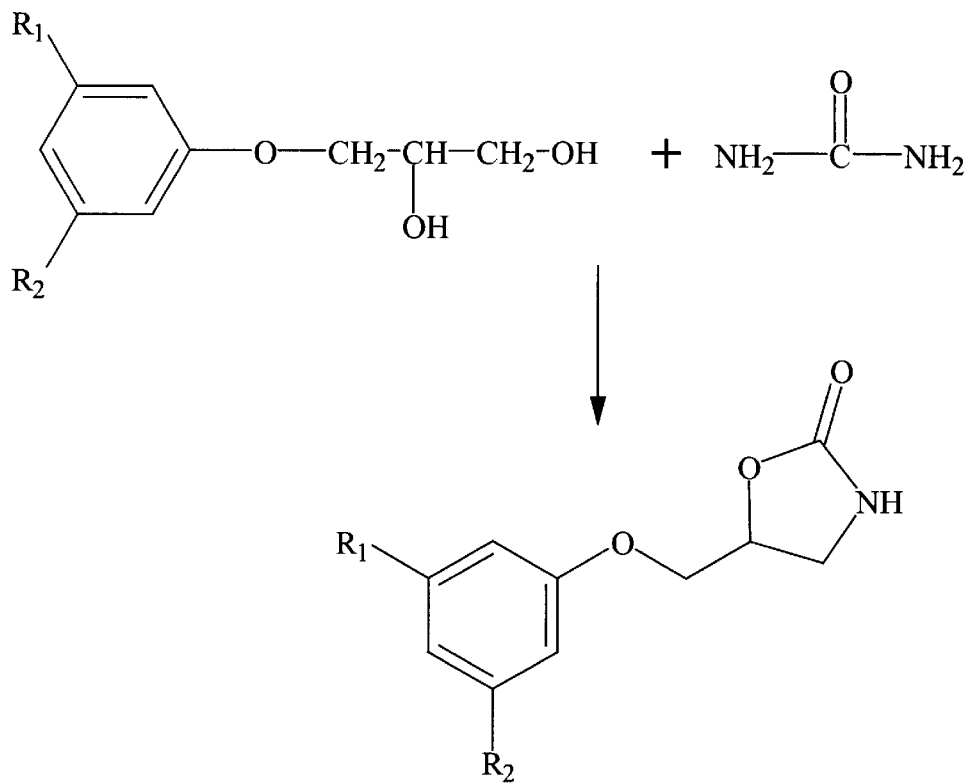
FIG. 2 (prior art) shows a reaction process for making 5-(3,5-dialylphenoxymethyl)-2-oxazolidinines. The reaction scheme is disclosed in U.S. Pat. No. 3,062,827. The reaction involves the fusion of a selected 3-phenoxy-1,2-propanediol (having the predetermined substituents on the phenyl rign) and urea in an approximately 1:2 molar ratio, by heating at an elevated temperature, usually 170° C. to 200° C., and preferably at about 185° C., with or without a solvent, for at least three hours. On completion of the reaction, the crude oxazolidinone may be dissolved in a suitable solvent and recovered by partitioning between water and ethyl acetate. The ethyl acetate layer is dried over sodium sulfate and concentrated.
Figure 3:
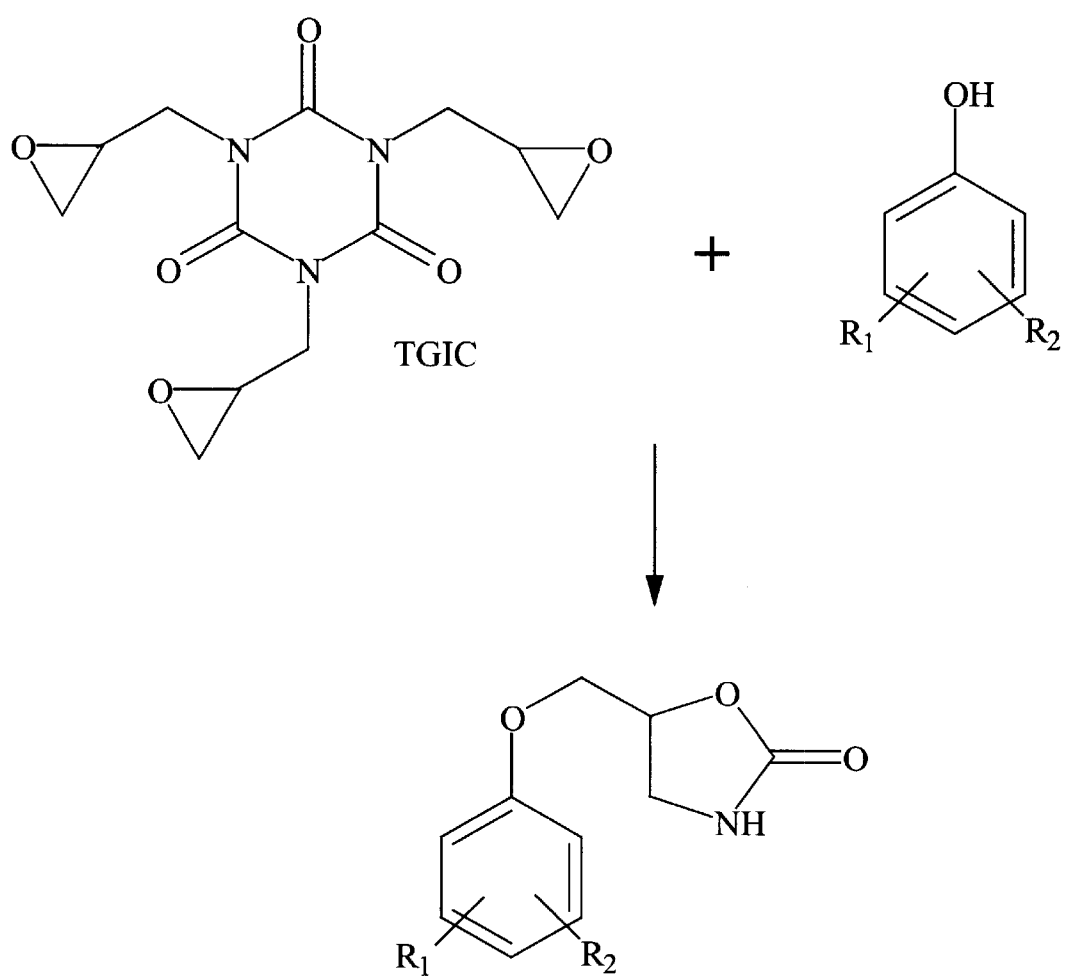
FIG. 3 shows the reaction scheme for making 5-aryloxymethyl-2-oxazolidinones in the present invention.

As shown in FIG. 3, the synthesis process of the present invention starts by refluxing the TGIC and the selected phenol. The reaction can be accomplished with or without a base, although the reaction is greatly improved in the presence of a base. Examples of the base include, but are not limited to, NaOH and $NH_4OH$. The preferred base is NaOH. The TGIC and the selected phenol are preferably dissolved in a solvent, such as acetone, ethyl alcohol, chloroform, and ethyl acetate. The preferred solvent is acetone. It can be used in combination with water.

The reaction is preferably under an anaerobic condition (such as under nitrogen). After the completion of the reaction, the solvent is removed by evaporation. The resulting crude oxazolidinone, in the form of a liquid, is purified by partitioning the crude oxaxolidinone between an organic solvent and water. Examples of the organic solvent include ethyl acetate and chloroform. The preferred organic solvent is ethyl acetate. The preferred volume ratio of the organic solvent and water is 50:30. After the layers are separated, the organic layer is collected and the water layer is removed and discarded.

The organic layer is then allowed to sit for a suitable amount of time until the purified oxazolidinone is precipitated. The precipitated oxazolidinone is then collected by filteration and dried, using conventional methods.

The following example is illustrative, but not limiting the scope of the present invention. Reasonable variations, such as those occur to reasonable artisan, can be made herein without departing from the scope of the present invention.

EXAMPLE

Synthesis of 5-(3,5-dimethylphenoxymethyl)-2-oxazolidinone

Ten (10) mmole of triglycidyl isocyanurate (TGIC), 30 mmole of 3,5-dimethylphenol, and 1.2 g of sodium hydroxide were dissolved in 50 mL of acetone. The reaction was carried out under refluxed condition and nitrogen overnight.

As indicated in FIG. 3, 1 mole of TGIC was reacted with 1–5 moles (preferably 3 moles) of the unsubstituted or substituted phenol in the presence of the base. Each of the $OH^-$ of the phenol interacted with one of the three epoxypropyl groups of the TGIC, which in turn interacted with the amido group on the isocyanurate to form an oxazolidinyl ring. The reaction yielded three moles of 5-aryloxymethyl-2-oxazolidinones.

At the end of the reaction, the solvent was evaporated to produce a liquid resultant containing the crude oxazolidinone. About 50 mL of ethyl acetate and 30 mL of water was then added to and mixed with the liquid crude oxazolidinone. When the ethyl acetate layer was completely separated from the water layer, the water layer was aspirated. The partitioning step was repeated twice, each by adding 30 mL of water to the remaining ethyl acetate layer, mixing the two layers, followed by phases separation and water removal by aspiration. The remaining ethyl acetate layer was allowed to sit for a suitable period of time. The precipitant was collected by filtration and dried using conventional methods.

The 5-(3,5-dimethylphenoxymethyl)-2-oxazolidinone produced by this method yielded about 1.8 g (81% yield), which was white, solid 5-(3,5-dimethylphenoxymethyl)-2-oxazolidinone powder.

The proton NMR chemical shifts and proton assignments of 5-(3,5-dimethylphenoxymethyl)-2-oxazolidinone in $CDCL_3$-d are showed in Table 1.

TABLE 1

$^1$H NMR of 5-(3,5-dimethylphenoxymethyl)-2-oxazolidinone in CDCL$_3$-d

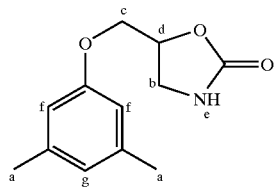

| chemical shift (ppm) | multiplicity | proton assignment | proton integration |
|---|---|---|---|
| 2.28 | singlet | a | 6 |
| 3.56–3.80 | multiplet | b | 2 |
| 4.12 | doublet (coupling constant: 4.8) | c | 2 |
| 4.88–4.98 | multiplet | d | 1 |
| 5.68 | singlet | e | 1 |
| 6.54 | singlet | f | 2 |
| 6.64 | singlet | g | 1 |

The carbon-13 NMR chemical shifts and carbon assignments of 5-(3,5-dimethylphenoxymethyl)-2-oxazolidinone in CDCL$_3$-d are shown presented in Table 2.

TABLE 2

$^{13}$C NMR of 5-(3,5-dimethylphenoxymethyl)-2-oxazolidinone in CDCL$_3$-d

| chemical shift (ppm) | carbon assignment |
|---|---|
| 21.36 | a |
| 42.76 | b |
| 67.88 | c |
| 74.20 | d |
| 112.42 | e |
| 123.40 | f |
| 139.41 | g |
| 158.18 | h |
| 159.33 | i |

The proton and carbon-13 NMR chemical shifts and chemical assignment results of Tables 1 and 2 confirmed the purity of the 5-(3,5-dimethylphoxymethyl)-2-oxazolidinone produced by the method described in the present invention.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A process for preparing a 5-aryloxymethyl-2-oxazolidinone of formula (I):

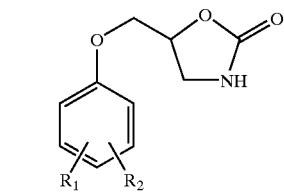

(I)

wherein R$_1$ and R$_2$ are hydrogen, halogen alkyl, or alkoxyl group; wherein said alkyl or alkoxyl group contains no more than 3 carbon atom in straight or branched chain;

said process comprising:
reacting a triglycidyl isocyanurate (TGIC) of formula (IV):

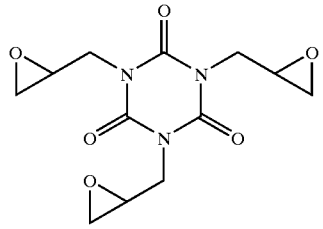

(IV)

with an unstituted or a substituted phenol of formula (V):

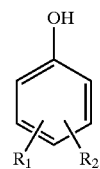

(V)

to produce said 5-aryloxymethyl-2-oxazolidinone;
wherein R$_1$ and R$_2$ are hydrogen, halogen, alkyl, or alkoxyl group; wherein said alkyl or alkoxyl group contains no more than 3 carbon atom in straight or branched chain.

2. The process according to claim 1, wherein said 5-aryloxymethyl-2-oxazolidinone is metaxolone.

3. The process according to claim 1, wherein said 5-aryloxymethyl-2-oxazolidinone is mephenoxalone.

4. The process according to claim 1, wherein said 5-aryloxymethyl-2-oxazolidinone is an antagonist of strychnine, an anticonvulsant, a skeletal muscle relaxant, or an anxiolytic.

5. The process according to claim 1, wherein said TGIC and said phenol are dissolved in a solvent.

6. The process according to claim 5, wherein said process is under reflux condition.

7. The process according to claim 5, wherein said solvent is at least one selected from the group consisting of acetone, ethanol, chloroform, and ethyl acetate.

8. The process according to claim 5, wherein said solvent is acetone or a combination of acetone and water.

9. The process according to claim 1, wherein said reaction is performed in the presence of a base.

10. The process according to claim 9, wherein said base is NaOH or NH$_4$OH.

11. The process according to claim 1, wherein said process is carried out under nitrogen.

12. The process according to claim 1, wherein said reaction is completed for a period of about 10–60 hours.

13. The process according to claim 1, wherein said reaction is completed for a period of about 12–24 hours.

14. The process according to claim 1, wherein said TGIC and said phenol or substituted phenol is at a molar ratio of about 1:1–1:5.

15. The process according to claim 1, wherein said TGIC and said phenol or substituted phenol is at a molar ratio of about 1:3.

16. The process according to claim 1, wherein said 5-aryloxymethyl-2-oxazolidinone is purified by:

partitioning said 5-aryloxymethyl-2-oxazolidinone between a water layer and an ethyl acetate layer;

recovering said purified 5-aryloxymethyl-2-oxazolidinone from said ethyl acetate layer.

17. The process according to claim 16, wherein said ethyl acetate layer and said water layer is at a volume ratio of 50:30.

* * * * *